United States Patent [19]
Thill

[11] Patent Number: 5,178,871
[45] Date of Patent: Jan. 12, 1993

[54] STABLE DOUBLE EMULSIONS CONTAINING FINELY-DIVIDED PARTICLES

[75] Inventor: Francis L. Thill, Burlington, Wis.

[73] Assignee: S. C. Johnson & Son, Inc., Racine, Wis.

[21] Appl. No.: 721,863

[22] Filed: Jun. 26, 1991

[51] Int. Cl.$^5$ ............................................. A01N 25/02
[52] U.S. Cl. .................... 424/405; 252/302; 252/304; 252/308; 252/315.01; 252/315.5; 252/315.6; 252/315.7; 424/45; 514/937; 514/938; 514/939; 514/941; 514/943
[58] Field of Search ............... 424/45, 405; 514/937, 514/938, 939, 941, 943; 252/302, 304, 308, 315.01, 315.5, 315.6, 315.7

[56] References Cited

U.S. PATENT DOCUMENTS

| | | |
|---|---|---|
| 2,022,246 | 11/1935 | Lindstaedt ............................ 514/762 |
| 2,075,359 | 3/1937 | Salzberg ................................ 514/63 |
| 2,219,287 | 10/1940 | Arnold .................................. 514/63 |
| 2,303,236 | 11/1942 | Shelton ................................ 514/762 |
| 2,681,878 | 6/1954 | Kauppi .................................. 514/63 |
| 2,711,987 | 6/1955 | Lyons .................................... 514/63 |
| 2,988,473 | 6/1961 | Mallis .................................... 514/63 |
| 3,030,266 | 4/1962 | Cuille ................................... 514/770 |
| 3,159,536 | 12/1964 | Marotta ............................... 424/600 |
| 3,240,670 | 3/1966 | Feinberg ................................ 424/91 |
| 3,291,687 | 12/1966 | Cranch ................................. 514/490 |
| 3,375,163 | 3/1968 | Whitney ................................ 514/63 |
| 3,392,040 | 7/1968 | Kass ................................ 106/287.13 |
| 3,647,861 | 3/1972 | Buchanan ............................ 560/153 |
| 3,898,277 | 8/1975 | Duerr .................................... 564/27 |
| 3,975,294 | 8/1976 | Dumoulin ........................... 252/354 |
| 3,997,492 | 12/1976 | Kane .................................... 524/801 |
| 4,017,615 | 4/1977 | Shastri ................................. 514/174 |
| 4,025,484 | 5/1977 | Evani et al. ......................... 523/400 |
| 4,080,190 | 3/1978 | Law ....................................... 71/67 |
| 4,115,098 | 9/1978 | Stull ................................ 514/938 X |
| 4,146,618 | 3/1979 | Sauers .................................. 514/63 |
| 4,155,995 | 5/1979 | Heinz .................................... 514/63 |
| 4,234,573 | 11/1980 | Boger ................................... 514/63 |
| 4,254,104 | 3/1981 | Suzuki ................................. 514/785 |
| 4,264,606 | 4/1981 | Ozawa .................................. 514/63 |
| 4,350,605 | 9/1982 | Hughett .............................. 252/305 |
| 4,360,517 | 11/1982 | Acker ................................... 514/63 |
| 4,385,049 | 5/1983 | Cuca .................................... 514/786 |
| 4,600,584 | 7/1986 | Friemel ............................... 424/601 |
| 4,632,827 | 12/1986 | Schlosser ............................. 514/63 |
| 4,654,328 | 3/1987 | Itoh ...................................... 514/63 |
| 4,663,314 | 5/1987 | Hayase ................................. 514/63 |
| 4,668,666 | 5/1987 | Allan .................................... 514/63 |
| 4,725,418 | 2/1988 | Friemel ............................... 423/305 |
| 4,775,664 | 10/1988 | Schubert ............................. 514/63 |
| 4,782,095 | 11/1988 | Gum .................................... 514/937 |
| 4,788,001 | 11/1988 | Narula ................................ 252/312 |
| 4,795,640 | 1/1989 | Helfenberger ...................... 424/405 |
| 4,931,210 | 6/1990 | Takahashi et al. ............. 514/937 X |
| 4,985,250 | 1/1991 | Bee et al. ............................ 424/401 |
| 5,017,605 | 5/1991 | Stindl ................................. 514/529 |
| 5,073,298 | 12/1991 | Gentle et al. ...................... 252/358 |

OTHER PUBLICATIONS

Condensed Chemical Dictionary 10th Edition published in 1981 by Van Nostrand Reinhold Company.
Handbook of Chemical Synonyms and Trade Names 8th Edition published in 1978 by the CRC Press, Inc.
Pesticides Theory and Application by George W. Ware published in 1983 by W. H. Freeman and Company.
"The Merck Index", 10th edition, published 1983 by Merck & Co., Inc.
Encyclopedia of Chemical Technology, 3rd edition, vol. 1., published 1978 by John Wiley & Sons, Inc.
Certain trade literature of Exxon Chemical.
Selected pages from "McCutcheon's".

Primary Examiner—Thurman K. Page
Assistant Examiner—Robert H. Harrison

[57] ABSTRACT

A preferred method of producing an aqueous, stable double emulsion is disclosed. The first step of the method is the production of an "inner" emulsion. The inner emulsion is produced by combining water, a liquid hydrocarbon solvent, and an emulsifier, in an agitated mixing vessel, along with an effective amount of finely-divided particulate material, to produce an oil-in-water emulsion having a viscosity of no more than about 200,000 centipoises, wherein the finely-divided particulate material is substantially homogeneously-dispersed throughout the thus-produced oil-in-water emulsion. The second step of the method is the production of an "outer" emulsion. The outer emulsion is produced by combining a liquid hydrocarbon solvent, water, and an emulsifier, in an agitated mixing vessel, to produce a water-in-oil emulsion. The third step of the method is the production of a "dual" emulsion. The dual emulsion is produced by combining the water-in-oil emulsion with an effective amount of the oil-in-water emulsion, in a mixing zone, thereby to produce the aqueous, stable double emulsion.

4 Claims, No Drawings

STABLE DOUBLE EMULSIONS CONTAINING FINELY-DIVIDED PARTICLES

TECHNICAL FIELD

The present invention, in general, is directed both to a method (or process) for producing stable, aqueous "double" emulsions (that are so prepared as to contain homogeneously-dispersed finely-divided solid particles therein) as well as to the novel stable, aqueous double emulsions produced thereby.

BACKGROUND ART

When it is desirable for liquid formulations containing solid particulate matter to be homogeneous, it may be necessary that the individual particles of the solid particulate matter be finely-divided or "powdery". However, liquid formulations containing this sort of solid particulate matter may quickly stratify and/or agglomerate, with the result typically being the settling-out of the particulate material. Or the liquid formulation may exhibit still other undesirable aspects of instability such as precipitation of agglomerated or individual particles.

To provide desired shelf-life or stability, it is often necessary to include certain stability-enhancing additives or dispersants—such as certain natural gums, certain minerals, or certain water-soluble polymers—to these sorts of liquid formulations. Carboxymethyl cellulose, polyvinyl alcohol, and certain vinyl polymers (e.g. "CARBOPOL") are illustrative of certain water-soluble polymers that can be utilized as dispersants in this regard. Suitable, illustrative natural gums include arabic, guar, karaya, and tragacanth. (See, e.g., page 513 of *The Condensed Chemical Dictionary*, 10th edition, published in 1981 by Van Nostrand Reinhold Co.) Suitable, illustrative minerals include "Jeweller's Rouge", which is a mineral-art term that is understood to mean either fine, calcined ferric oxide or "haematite." (See, e.g., page 390 of the *Handbook of Chemical Synonyms and Trade Names*, 8th edition, published in 1978 by the CRC Press, Inc.) "Haematite", in turn, is a mineral-art term that is understood to refer to certain varieties of naturally-occurring, anhydrous ferric oxide. (See, e.g., page 343 of the *Handbook of Chemical Synonyms and Trade Names*, 8th edition.)

The use of particulate dispersants (such as the above-noted) to produce "stable" emulsions containing finely-divided particles can result in a number of undesirable side effects, however. For example, the natural gums as well as certain water-soluble polymeric dispersants may typically leave a "gummy" residue that can readily attract dirt. Moreover, the "Jeweller's Rouge" can be difficult to remove and thus may give rise to unsightly discoloration if left on a particular substrate surface over an extended period of time.

Other naturally-occurring minerals that can be used as dispersants, to produce so-called "stable" emulsions include, e.g., attapulgite, bentonite, clay, and fuller's earth. (See, e.g., pages 95, 115, 255, and 481, respectively, of the *The Condensed Chemical Dictionary*, 10th edition.) Naturally-occurring minerals of these sorts, however, typically may leave an unsightly or otherwise undesirable "scum" on a particular surface.

Thus to achieve overall acceptability for a wide variety of consumer and industrial uses, it is desirable to be able to produce stable liquid formulations without resorting to the inclusion of those sorts of stability-enhancing additives or dispersants mentioned hereinabove.

Yet it is particularly desirable that a wide variety of such liquid formulations—i.e., those which do not include the sorts of stability-enhancing additives or dispersants that are mentioned hereinabove—not only contain finely-divided particles homogeneously-dispersed throughout but that such liquid formulations also possess desirable shelf-life and other desirable "stability" qualities as well.

SUMMARY DISCLOSURE OF INVENTION

Accordingly, one aspect of my invention is summarized in the following description of a method for producing my novel aqueous stable double emulsion. My method includes several steps. The first step of my method is the production of a so-called "inner" emulsion. The inner emulsion is produced by combining water, a suitable liquid hydrocarbon solvent, and a suitable emulsifier (or surfactant), in an agitated mixing vessel of suitable size, along with an effective amount of a suitable finely-divided particulate material, to produce an oil-in-water emulsion having a viscosity of no more than about 200,000 centipoises ("cPs."), wherein the finely-divided particulate material is substantially homogeneously-dispersed throughout the thus-produced oil-in-water emulsion.

The second step of my method is the production of a so-called "outer" emulsion. The outer emulsion is produced by combining a suitable liquid hydrocarbon solvent, water, and a suitable emulsifier (or surfactant), in an agitated mixing vessel of suitable size, to produce a water-in-oil emulsion. (The liquid hydrocarbon solvent and emulsifier may be the same as or may differ from what was used in the first step.)

The third step of the method is the production of a so-called "dual" emulsion. The dual emulsion is produced by combining the water-in-oil emulsion (produced via the second step) with an effective amount of the oil-in-water emulsion (produced via the first step), in a mixing zone, to produce my novel aqueous stable double emulsion, which also can be characterized as a stable dual emulsion.

Other aspects and features of my present invention will be discussed in greater detail further hereinbelow.

INDUSTRIAL APPLICABILITY

The stable double emulsions of my invention can be used in a wide variety of applications and thus will be utilized in conjunction with various formulations, compositions-of-matter, and so forth, depending upon desired end-use.

For example, suitable surface-coating ingredients can be incorporated into one particular embodiment of my invention that is characterized as a stable double emulsion-containing formulation, to produce a wide assortment of surface coatings and/or films, as desired. As a particularly preferred example, suitable insecticidally-active or insect-repellent ingredients can be incorporated into my stable double emulsion formulation, to produce a variety of insecticides or repellents, whichever is desired.

As still another example, the finely-divided particulate material can be faujasite, molecular sieves, or another suitably absorptive material; and an effective amount of such a finely-divided absorptive material can be incorporated into my stable double emulsion formulation, for purposes of producing odor-adsorbing compositions-of-matter. Still further, a particulate material having a predetermined "abrasive" value or index can be selected and thereafter rendered finely-divided to a suitable particle-size range for subsequent incorporation into my stable double emulsion formulation, for purposes of producing a wide assortment of desired polishing compositions.

BEST MODE FOR CARRYING OUT THE INVENTION

As was briefly mentioned above, the first step of my novel method is the production of a so-called "inner" emulsion. The inner emulsion is produced by combining water, a suitable liquid hydrocarbon solvent, and a suitable emulsifier (or surfactant), in an agitated mixing vessel of suitable size, along with an effective amount of a suitable finely-divided particulate material, to produce an oil-in-water emulsion having a viscosity of no more than about 200,000 centipoises ("cPs."), wherein the finely-divided particulate material is substantially homogeneously-dispersed throughout the thus-produced oil-in-water emulsion.

For purposes of my present invention, suitable liquid hydrocarbon solvents include but are not limited to aliphatic, aromatic, cyclic, and various mixtures of commercially available hydrocarbon solvents. Those skilled in the art are readily able to choose a particular hydrocarbon solvent for a desired end-use. My preferred end-use, for example, is in connection with the production of insecticidal formulations and insect-repellent formulations. In that regard, preferred commercially available hydrocarbon solvents include but are not limited to naphthas having a boiling point range of 93 degrees Celsius ("°C.") to more than 300° C., preferably about 180° C. to about 300° C.; liquid isoparaffinic and normal paraffinic solvents such as those presently commercially available from Exxon Chemicals of Houston, Tex., under the "ISOPAR" and "NORPAR" brand names; and mineral oil. Particularly preferred is "white oil" (See, e.g., page 1096 from *The Condensed Chemical Dictionary*, 10th edition.) Preferred "ISOPAR" brand solvents include "ISOPAR C", "ISOPAR E", "ISOPAR G", "ISOPAR H", "ISOPAR K", "ISOPAR L" and "ISOPAR M"

For purposes of my present invention, various emulsifiers (also called surfactants) may be used. For example, various amphoteric, anionic, cationic, and/or nonionic emulsifiers may be used. Of these, I prefer to use nonionic emulsifiers. Accordingly, nonionic emulsifiers that would be suitable for purposes of my invention include ethoxylated fatty acids, ethoxylated fatty-acid esters, ethoxylated fatty alcohols, glycol esters, propoxylated fatty acids, propoxylated fatty-acid esters, propoxylated fatty alcohols, glycerol esters, sorbitan esters, ethoxylated sorbitan esters, sarcosine derivatives, and combinations thereof. Of these, preferred nonionic emulsifiers include sorbitan monostearate, sorbitan monoisostearate, sorbitan monooleate, POE (20) sorbitan monostearate, POE (20) monooleate, POE (3) oleic acid, POE (3) stearic acid, and combinations thereof.

For purposes of my present invention, suitable particulate materials include but are not limited to activated charcoal, calcined alumina, calcined ferric oxide, calcium metasilicate, calcium carbonate, diatomaceous silica, fumed silica, amorphous silica, hydrous magnesium silicate, hydrous aluminum silicate, anhydrous aluminum silicate, and combinations thereof. Particularly preferred is a micro silica having a particle size of about 0.01 microns to about 25 microns, an "apparent" bulk density of less than 21.0 pounds per cubic foot, and a surface area of about 275 square meters per gram to about 320 square meters per gram.

Preferably, the oil-in-water emulsion, produced in accordance with the first step of my novel method will have a viscosity of no more than about 50,000 cPs. More preferably, the viscosity will be no more than about 20,000 cPs. Most preferably, the viscosity will be no more than about 10,000 cPs. All such viscosity measurements are determined at 25 degrees Celsius (77 degrees Fahrenheit).

As was also briefly mentioned above, the second step of my novel method is the production of a so-called "outer" emulsion. The outer emulsion is produced by combining a suitable liquid hydrocarbon solvent, water, and a suitable emulsifier (or surfactant), in an agitated mixing vessel of suitable size, to produce a water-in-oil emulsion.

The hydrocarbon solvent and emulsifier ingredients mentioned above in connection with the first step are suitable for purposes of production of the water-in-oil ("outer") emulsion of the second step. Preferred physical properties of the "outer" emulsion are to possess a viscosity of between 1.0 cPs to 20,000 cPs. at 25° C., and contain a minimum of 1.0 weight percent ("wt.-%") water to a maximum of 50.0 wt.-% water.

As was further briefly mentioned above, the third step of my novel method is the production of a so-called "dual" emulsion. The dual emulsion is produced by combining the water-in-oil emulsion with an effective amount of the oil-in-water emulsion, in a mixing zone, to produce my novel aqueous double emulsion, which also can be characterized as a stable dual emulsion. Preferred physical properties of my dual emulsion (which is a water-in-oil emulsion) are that the emulsion possess a viscosity of about 100 cPs. to 20,000 cPs. at 25° C., and contain a minimum of about 10 wt.-% water to a maximum of about 60.0 wt.-% water. In that regard, to produce my novel aqueous double emulsion, 0.01 parts-by-weight to about 200 parts-by-weight of the oil-in-water emulsion are combined with 100 parts-by-weight of the water-in-oil emulsion, preferably 0.1 parts-by-weight to about 100 parts-by-weight of the oil-in-water emulsion are combined with 100 parts-by-weight of the water-in-oil emulsion, more preferably about 1 part-by-weight to about 50 parts-by-weight of the oil-in-water emulsion are combined with 100 parts-by-weight of the water-in-oil emulsion, and most preferably about 30 parts-by-weight of the oil-in-water emulsion are combined with 100 parts-by-weight of the water-in-oil emulsion.

As the term "stability" is used in this disclosure, the term connotes that finely-divided particulate material does not settle out of the emulsion, when stored at a temperature range of from about 10° C. to about 30 degrees Celsius, even after being thus stored for 1 year.

DETAILED DESCRIPTION OF EXAMPLES

The following examples are set forth to illustrate more clearly, to those skilled in the art, the various principles and practice of this particular invention. Yet as such, they are not intended to limit my invention but rather are merely illustrative of the so-called "best mode" aspects and/or features of my invention, and as such are thus characterized as preferred embodiments.

EXAMPLE 1

Preferred Method Of Producing Inner Emulsion

The inner emulsion is an oil-in-water ("O/W") emulsion. Those skilled in the art of emulsion technology also refer to oil-in-water emulsions as "water out" emulsions.

The preferred ingredients of the inner emulsion are set forth in Table I, below.

TABLE I

| Inner Emulsion Ingredients | | |
|---|---|---|
| Ingredients | Function | Parts |
| Water | Continuous Phase | 78.90 |
| Hydrocarbon Solvent | Discontinuous Phase | 16.00 |
| Micro-Silica | Finely-Divided Particulate Material | 4.00 |
| Sorbitan Monooleate | Nonionic Emulsifier | 0.75 |
| POE (20) Sorbitan Monooleate | Nonionic Emulsifier | 0.25 |
| Sodium Nitrite | Corrosion Inhibitor | 0.10 |

In Table I, the term "parts" means parts-by-weight. Also, the hydrocarbon solvent utilized, more particularly characterized as a mixture of naphthenes and normal paraffins, was "EXXSOL D 60" (brand) hydrocarbon solvent mixture, available from ESSO Chemicals of Toronto, Ontario, Canada. The finely-divided particulate material utilized, perhaps more precisely characterized as a micro-silica having a particle size of about 0.01 to about 25 microns, an apparent bulk density of less than 21.0 pounds per cubic foot (i.e., less than about 1.31 kilograms per cubic meter) and an apparent surface area of about 275 to about 320 square meters per gram, was "SYLOID 620" (brand) micro-silica, available from Davison Chemical, a W. R. Grace division, of Baltimore, Md.

Preferably, two somewhat different nonionic, sorbitan monooleate-based emulsifiers (or surfactants) were utilized. One such nonionic emulsifier, generically simply referred to as liquid sorbitan monooleate and having an "HLB" value of 4.3 is commercially available from ICI Americas, Inc., of Wilmington, Del., under the "SPAN 80" brand name. The other nonionic emulsifier, more particularly referred to as liquid POE (20) sorbitan monooleate and having an "HLB" value of 15.0 is commercially available from ICI Americas, Inc., under the "TWEEN 80" brand name. (See, e.g., pages 167-168 and 196-197, respectively, of "McCutcheon's" *Emulsifiers & Detergents*, North American Edition, published in 1990 by MC Publishing Co. of Glen Rock, N.J.) Those skilled in the art of emulsion technology are well aware that the term "HLB" value is more precisely referred to as the hydrophile-lipophile balance value. (See, e.g., U.S. Pat. No. 3,997,492 to Kane et al.)

Lastly, sodium nitrite, an optional ingredient, was used to inhibit the otherwise somewhat corrosive nature of the inner emulsion with respect to subsequent containment by a metal container.

My preferred method of producing the inner emulsion will now briefly be described.

First, I combined water, which I had pre-heated to a desired elevated temperature of about 49 degrees Celsius (about 120 degrees Fahrenheit), with sodium nitrite, in a mixing vessel of suitable size to produce a corrosion inhibitor-containing aqueous mixture (at the desired elevated temperature), utilizing moderate agitation. Then, I combined the two nonionic emulsifiers along with the above-noted hydrocarbon solvent mixture into a separate mixing vessel of suitable size, utilizing moderate agitation while similarly heating to the desired elevated temperature of about 49 degrees Celsius, to produce an emulsifier-containing liquid hydrocarbon solvent mixture. Next, I introduced the liquid hydrocarbon mixture into the aqueous mixture, utilizing moderate agitation while maintaining the desired elevated temperature, to produce an oil-in-water emulsion. Then, utilizing relatively high-shear agitation while still maintaining the desired elevated temperature, I incorporated the finely-divided particulate material into the oil-in-water emulsion, thereby producing an oil-in-water emulsion having a viscosity of about 1000 centipoises ("cPs.") and containing the micro-silica substantially homogeneously-dispersed throughout.

Thereafter, I cooled the particulate material-containing emulsion to a temperature of about 25 degrees Celsius (77 degrees Fahrenheit) for subsequent use in connection with Example 3, below. In particular, the Example 1 emulsion was utilized as a so-called "inner" emulsion in combination with the so-called "outer" emulsion of Example 2 (also discussed below), to produce the "dual" emulsion of Example 3.

EXAMPLE 2

Preferred Method Of Producing Outer Emulsion

The outer emulsion is a water-in-oil ("W/O") emulsion. Those skilled in the art of emulsion technology also refer to water-in-oil emulsions as "oil out" emulsions. The Example 2 water-in-oil emulsion was preferably so formulated as to include certain insecticidally-active ingredients. The Example 3 dual emulsion (discussed in greater detail below) includes the Example 1 inner emulsion and the Example 2 outer emulsion.

The preferred ingredients of the outer emulsion, together with the Example 1 inner emulsion (which is listed as one of the various ingredients of the dual emulsion), are set forth in Table II, below.

TABLE II

| Dual Emulsion Ingredients | | |
|---|---|---|
| Ingredients | Function | Parts |
| Hydrocarbon Solvent | Continuous Phase | 39.295 |
| Ex. 1 Emulsion | Inner Emulsion | 32.210 |
| Water | Discontinuous Phase | 18.344 |
| Piperonyl Butoxide | Synergist | 3.221 |
| Isoparaffinic Solvent | Diluent | 2.577 |
| Sorbitan Monooleate | Nonionic Emulsifier | 1.530 |
| 3.5 ETO Stearic Acid | Nonionic Emulsifier | 1.530 |
| Permethrin | Active Ingredient | 0.673 |
| Florasynth LA 78-1210 | Fragrance | 0.320 |
| Pyrethrin | Active Ingredient | 0.200 |
| Sodium Nitrite | Corrosion Inhibitor | 0.100 |

In Table II, the term "parts" means parts-by-weight. Also, "EXXSOL D 60" (brand) liquid hydrocarbon solvent (described above) was utilized as the "continuous phase" portion of the water-in-oil emulsion of Example 2. The above-described oil-in-water emulsion of Example 1 was incorporated into the water-in-oil emulsion of Example 2 (to produce the dual emulsion of Example 3), as will be described in detail below.

Water was utilized as the "discontinuous phase" portion of the water-in-oil emulsion of Example 2. Piperonyl butoxide was utilized as a synergist for the pyrethrin. The term "synergism" is understood to refer to a chemical phenomenon in which the effect of two active components of a mixture is more than additive. (See, e.g., page 988 of *The Condensed Chemical Dictionary*, 10th edition.) Indeed, it is well-known that a primary "use" for piperonyl butoxide is as a synergist in insecticides in combination with pyrethrums in oil solutions, emulsions, powders, or aerosols. (See, e.g., page 819 of *The Condensed Chemical Dictionary*, 10th edition.) "ISOPAR M" (brand) liquid isoparaffinic solvent was utilized as a diluent for the pyrethrin.

"ISOPAR M" isoparaffinic solvent has a Kauributanol value of 27, a typical flash point of about 77 degrees Celsius to about 80 degrees Celsius (about 170 degrees Fahrenheit to about 176 degrees Fahrenheit), and an auto ignition temperature of 338 degrees Celsius (about 640 degrees Fahrenheit). Additional technical information concerning "ISOPAR M" (brand) liquid isoparaffinic solvent can be found in a brochure entitled "ISOPAR", published in 1983 by the Exxon Chemicals of Houston, Tex. See also a product data sheet, identified as "DG-1P", entitled "ISOPAR M", and published in 1978.

In the preferred preparation of the Example 2 emulsion, two different nonionic emulsifiers (or surfactants) were utilized. One such emulsifier, namely "SPAN 80" (brand) sorbitan monooleate is described hereinabove in connection with Example 1. The other emulsifier, identified in Table II (above) as 3.5 ETO stearic acid, is available under the "TRYDET 26" (brand) name, from the Emery Group of Henkel Corporation of Cincinnati, Ohio. (See, e.g., pages 195-196 of "McCutcheon's" *Emulsifiers & Detergents*, North American edition, published in 1990.)

The Example 2 emulsion also preferably included two insecticidally-active ingredients. Permethrin, a synthetic pyrethroid, was utilized as one such insecticidally-active ingredient. Other well-known synthetic pyrethroids include fenvolerate, allethrin, tetramethrin, resmethrin, bioresmethrin, d-trans-allethrin, and phenothrin. (See, e.g. pages 56-57 of "Pesticides" *Theory and Application*, by George W. Ware, published in 1983 by W. H. Freeman and Company.) The particular permethrin identified in Table II (above) is available under the "Pounce Technical" (brand) name, as a 90.0 weight percent "actives" liquid, from Fairfield-American (FMC), of Philadelphia, Pa.

The other insecticidally-active ingredient presented in Table II is a naturally-occurring pyrethrin, presently commercially-available from the so-called "Py Board" of Kenya, as a 54 weight-percent "actives" liquid.

Also, Florasynth LA 78-1210 (brand) fragrance, available from Florasynth, Inc., of New York, N.Y., was utilized as still another optional ingredient in preparation of the Example 2 emulsion.

Lastly, sodium nitrite, also an optional ingredient, was utilized to inhibit the otherwise somewhat corrosive nature of the outer emulsion with respect to subsequent containment by a metal container.

My preferred method of producing the outer emulsion will now briefly be described.

First, I combined the liquid hydrocarbon solvent, the synergistic ingredient, the emulsifiers, the isoparaffinic diluent, the active ingredients, and the fragrance in a mixing vessel of suitable size and, while maintaining moderate agitation, heated the resultant "continuous phase" mixture to achieve a desired temperature of between 57 degrees Celsius (135 degrees Fahrenheit) and 66 degrees Celsius (150 degrees Fahrenheit). The isoparaffinic diluent, an optional ingredient, is used to "cut" (i.e., dilute) the naturally-occurring active ingredient, pyrethrin, presented above in Table II.

Then, in a separate mixing vessel of suitable size, I combined the water and sodium nitrite and, while maintaining moderate agitation, heated the resultant "discontinuous phase" mixture to achieve a desired temperature of between 60 degrees Celsius (140 degrees Fahrenheit) and 66 °C. Next, while maintaining the desired temperature of the "continuous phase" mixture, I added the "discontinuous phase" mixture into the "continuous phase" mixture, utilizing relatively high-shear agitation, thereby producing a water-in-oil emulsion, the so-called "outer" emulsion of Example 2.

EXAMPLE 3

Preferred Method Of Producing Dual Emulsion

Then, into this outer emulsion (of Example 2), in an agitated mixing vessel of suitable size, I slowly added the inner emulsion of Example 1, over a time period of about 2 to about 5 minutes, utilizing relatively high-shear agitation, to produce the dual emulsion (of Example 3). Finally, I homogenized the dual emulsion (which is a preferred step of mine) and thereafter cooled the now-homogenized dual emulsion to room temperature, before transferring to a suitable site for further processing. The term "room temperature" is understood to mean an interior temperature of from about 20 degrees Celsius to about 25 degrees Celsius, i.e., about 68 degrees Fahrenheit to about 75 degrees Fahrenheit. (See, e.g , page 899 of *The Condensed Chemical Dictionary*, 10th edition.)

EXAMPLE 4

Preferred Aerosol Formulation

A preferred method of utilizing my dual emulsion to produce an aerosol formulation will now be described. The various aerosol formulation ingredients are set forth in Table III, below.

TABLE III

| Aerosol Formulation Ingredients | | |
| --- | --- | --- |
| Ingredients | Function | Parts |
| Water | Discontinuous Phase | 46.85 |
| Dual Emulsion (Ex. 3) | Continuous Phase | 31.05 |
| A-60 | Propellant | 22.00 |
| Sodium Nitrite | Corrosion Inhibitor | 0.10 |

Into a cylindrical, metal pressure container of suitable size was added 46.85 parts-by-weight of water and 0.10 parts-by-weight of the corrosion inhibitor, sodium nitrite. Also added into the metal pressure container were 31.05 parts-by-weight of the dual emulsion of Example 3 as well as 22.00 parts-by-weight of "A-60" propellant. The metal pressure container was then sealed and equipped with suitable aerosol valve components, well known to those skilled in the art. (See, e.g., pages 592-596 of the "Kirk-Othmer" *Encyclopedia Of Chemical Technology*, 3rd edition, volume 1, published in 1978 by John Wiley & Sons, Inc.)

The propellant listed above in Table III and identified as "A-60" has a vapor pressure of about 60 pounds per square inch gauge ("p.s.i.g."), i.e., 413.7 kilopascals ("kPa."). "A-60" propellant comprises about 47 mole percent propane and about 53 mole percent n-butane.

Thus, my novel dual emulsion can be combined with an optional propellant ingredient, for purposes of producing an aerosol formulation.

Normally, the optional propellant ingredient is so chosen as to be immiscible with the aqueous phase; but it need not be. In particular, certain water-soluble propellants, such as dimethyl ether (DME), are suitable for purposes of my present invention. Additional suitable water-soluble or partially water-soluble propellants include nitrous oxide (which is moderately soluble in water), as well as carbon dioxide (which is soluble in water in only very minute concentrations).

Additional suitable propellants, for purposes of my present invention, include, but are not limited to, certain liquefied and compressed gases. Suitable liquefied gases, for purposes of my present invention, include a wide variety of known hydrocarbon propellants (such as various $C_1$ to $C_4$ hydrocarbons).

Illustrative of the preferred hydrocarbon propellants are propane, n-butane, isobutane, and various mixtures thereof. Additional suitable compressed gases, for purposes of the present invention, include air and nitrogen.

One well-known, presently preferred propellant, often referred to as "A-46" by those skilled in the art, has a vapor pressure of about 46 p.s.i.g. (317.2 kPa.) and comprises about 80 mole percent isobutane and about 20 mole percent propane. Another well-known presently preferred propellant, referred to as "A-31" by those skilled in the art, is isobutane.

In the aerosol formulation presented in Table III (above), the optional ingredient sodium nitrite is included as a corrosion inhibitor. Additional, suitable metal-corrosion inhibitors, for purposes of my present invention, include sodium benzoate and the mixture comprising sodium benzoate and sodium nitrite.

In addition to the ingredients identified in Table III (above), the aerosol formulation can further optionally include a fragrance and/or a microorganism growth inhibitor (or so-called "preservative"), if desired. One such illustrative microorganism growth inhibitor (or preservative) is formaldehyde. One particularly suitable preservative, well-known by its brand name of "Kathon", is commercially available from Rohm & Haas Co.

EXAMPLE 5

Preferred Insecticidal Formulation

The formulation presented below in Table IV, which is a presently preferred insecticidally-active formulation, was prepared by methods described hereinabove (in Examples 1-3), as can be appreciated by those skilled in the art.

TABLE IV

| Insecticidally-Active Formulation | | |
|---|---|---|
| Ingredients | Function | Parts |
| Water | Discontinuous Phase | 59.693 |
| A-60 | Propellant | 22.000 |
| Hydrocarbon Solvent | Continuous Phase | 15.105 |
| Micro-Silica | Finely-Divided Particulate Material | 1.400 |
| Sorbitan Monooleate | Nonionic Emulsifier | 0.550 |
| 3.5 ETO Stearic Acid | Nonionic Emulsifier | 0.475 |
| Permethrin | Active Ingredient | 0.188 |
| Tetramethrin | Active Ingredient | 0.188 |
| Piperonyl Butoxide | Synergist | 0.188 |
| Florasynth LA 78-1210 | Fragrance | 0.100 |
| Sodium Nitrite | Corrosion Inhibitor | 0.088 |
| POE (20) Sorbitan Monooleate | Nonionic Emulsifier | 0.025 |

Additional comments relating to the above-listed ingredients of Table IV includes the following. The water also functions as a diluent for the Table IV formulation. The "A-60" propellant is described above in connection with Table III. The hydrocarbon solvent utilized, "EXXSOL D 60", is described above in connection with Tables I and II; such a hydrocarbon solvent was utilized to produce a dual emulsion, as is described above in connection with Tables II and III. The micro-silica utilized, "SYLOID 630", is described above in connection with Table I. The sorbitan monooleate nonionic emulsifier utilized, "SPAN 80", is described above in connection with Table I. The 3.5 ETO stearic acid nonionic emulsifier utilized, "TRYDET 26", is described above in connection with Table II. The permethrin and tetramethrin active ingredients are described above in connection with Table II, as is the piperonyl butoxide synergist. In Table IV, the permethrin, the tetramethrin and the piperonyl butoxide are collectively referred to as "actives" by those skilled in the art. The fragrance presented in Table IV, namely "Florasynth LA 78-1210", is discussed above in connection with Table II. The sodium nitrite corrosion inhibitor is described above in connection with Tables I through III. The POE (20) sorbitan monooleate nonionic emulsifier utilized, "TWEEN 80", is described above in connection with Table I.

Alternatively, the three "active" ingredients discussed above in connection with Table IV can be pre-blended with the micro-silica, utilizing equipment and techniques well-known to those skilled in the art, for purposes of preparing a relatively free-flowing powdery "actives"-containing material, if desired.

Moreover, in lieu of the "actives" described hereinabove, the formulation of my invention can include insecticides and/or acaricides as well as herbicides and/or plant-growth regulators, if desired. Suitable and well-known insecticides and acaricides for such a purpose are set forth at pages 241-259 of the text entitled Pesticides: *Theory And Application* by George W. Ware, published 1983 by W. H. Freeman and Company, San Francisco, Calif., U.S.A.; and suitable, well-known herbicides and plant-growth regulators for such a purpose are set forth at pages 260-270 of the Ware text.

In Table IV, the term "parts" means parts-by-weight. The insecticidal properties of the Table IV formulation as well as procedures utilized for purposes of determining the insecticidal properties are described as follows.

EXPERIMENTAL EQUIPMENT AND SUBJECT MATTER

Several glass or virgin-plywood panels, each having a surface area of about 36 square inches and each being free from insecticide contaminate, were obtained for purposes of performing certain efficacy experiments upon selected cockroach species. In particular, the cockroaches utilized were adult male German cockroaches, known to those skilled in the art as *Blattella germanica*.

EXPERIMENTAL PROCEDURES

Onto each selected one of the above-described panels was applied equal-weight dosages of the Example 5 formulation. In particular, about 0.5 grams of the Example 5 formulation was applied onto a selected glass panel, and about 1.0 gram of the Example 5 formulation was applied onto a selected plywood panel. Each panel was then "conditioned", at a temperature ranging between about 75-85 degrees Fahrenheit (about 24° C. to about 29° C.) and at a relative humidity ("R.H.") of about 40% minimum, for a minimum of eighteen (18) hours.

TEST PROTOCOL

The test protocol selected was utilized to determine "Speed-of-Residual Kill", which is a parameter well-known to those skilled in the art. In particular, the well-known, so-called "Walk Across" test, which characterized a cockroach response to a forced exposure to an aliquot sample of the Example 5 formulation, of 5.0 seconds, required that the German cockroaches be moved across the thus-treated surfaces. In this regard, twenty-five (25) German cockroaches were placed inside a covered cylinder measuring about 3.5 inches in diameter by about 3 inches high (and having lightly-greased inner sidewalls); and the German cockroaches were then caused to move across the thus-treated surface for each replicate. The thus-exposed German cockroaches were thereafter retained and observed for mortality, and the observation "counts" were made at 30 sec., 1.0 min., 1.5 min., 2.0 min., 2.5 min. and 3.0 min. intervals, to determine the percent knockdown ("Kd"). Finally, a twenty-four (24) hour "count", my final reading, presents still another well-known parameter in determining percent mortality and/or recovery. (One desirable objective of a number of commercial formulators is to develop formulations possessing minimal recovery after 24 hours.) After the insects were exposed to the thus-treated insecticidal surfaces, no food or water was made available to them.

The following data represents the average of five (5) replicates.

TABLE V

| Observed Average Percent Knockdown | | | | | | |
|---|---|---|---|---|---|---|
| After 0.5 min. | After 1.0 min. | After 1.5 min. | After 2.0 min. | After 2.5 min. | After 3.0 min. | After 24.0 Hours |
| 29% | 47% | 62% | 76% | 78% | 80% | 64% |

Other toxicants suitable for purposes of inclusion in the composition-of-matter of my present invention are well-known in the art. Moreover, the stable double emulsion of my present invention can include a toxicant having a delayed effect (which is useful in controlling social insects such as ants), or the stable double emulsion can include a toxicant having an immediate effect (which is generally useful in controlling a wide variety of crawling arthropods). Such well-known toxicants include, but are not limited to, a variety of commercially-available organic compound-based toxicants, including organo phosphorus compounds, and carbamates as well as inorganic toxicants and insect growth regulators. (See, for example, the above-mentioned text entitled "Pesticides: Theory and Application" by George W. Ware, published in 1983 by W. H. Freeman and Company.)

For purposes of my present invention suitable organo phosphorus compounds include phosphates, phosphonothionates and phosphorothionates. For example, suitable, well-known organo phosphorus compounds, useful as toxicants in my present invention, include but are not limited to: acetyl phosphoramido thioic acid O,S-dimethyl ester, also known by its so-called "trivial" name of "Acephate", and commercially available under the "Ortho" and "Orthene" (brand) names (see also U.S. Pat. Nos. 3,716,600 and 3,845,172, both to Chevron); phosphoro thioic acid O,O-diethyl O-(3,5,6-trichloro-2-pyridinyl) ester, also known by its "trivial" name of "Chlorpyrifos", and commercially available under the "Dursban", "Lorsban", and "Pyrinex" (brand) names (see also U.S. Pat. No. 3,244,586 to Dow); phosphoro thioic acid O,O-diethyl O-[6-methyl-2-(1-methylethyl)-4-pyrimidinyl]ester, also known by its "trivial" name "Dimpylate", and commercially available under the "Basudin", "Diazinon", "Diazol", "Garden Tox", "Sarolex", and "Spectracide" (brand) names (see also U.S. Pat. No. 2,754,243 to Geigy); phosphoro thioic acid O,O-dimethyl O-(3-methyl-4-nitrophenyl) ester, also known by its "trivial" name of "Fenitrothion", and commercially available under the "Accothion", "Cyfen", "Cyten", "Folithion", "MEP", "Metathion" and "Sumithion" (brand) names (see also Belgian Pat. No. 594,669 to Sumitomo as well as Belgian Pat. No. 596,091 to Bayer); phosphoro thioic acid O,O-dimethyl O-[3-methyl-4-(methylthio)phenyl]ester, also known by its "trivial" name of "Fenthion", and commercially available under the "Baycid", "Baytex", "Entex", "Lebaycid", "Mercaptophos", "Queletox", "Spotton", "Talodex" and "Tiguvon" (brand) names (see, e.g., German Pat. No. 1,116,656 as well as U.S. Pat. No. 3,042,703, both to Bayer; see also Japanese Pat. No. 15,130, which issued in 1964 to Sumitomo); 4-ethoxy-7-phenyl-3,5-dioxa-6-aza-4-phosphaoct-6-ene-8-nitrile 4-sulfide, also known by its "trivial" name of "Phoxim", and commercially available under the "Baythion", "Sebacil" and "Volaton" (brand) names (see also U.S. Pat. No. 3,591,662 to Bayer); and the O,O-dimethyl analog of O-[2-(diethylamino)-6-methyl-4-pyrimidinyl]-phosphoro thioic acid O,O-diethyl ester, also known as its "trivial" name of "Pirimiphos-methyl", and commercially available under the "Actellic", "Blex", and "Silo San" (brand) names. (See, e.g., entry numbers 25, 2167, 2968, 3910, 3927, 7251 and 7372, respectively, in a text entitled "The Merck Index", 10th ed., published in 1983 by Merck & Co., Inc.)

For purposes of my present invention suitable carbamates include but are not limited to: 2,2-dimethyl-1,3-benzodioxol-4-ol methyl carbamate, also known by its "trivial" name of "Bendiocarb", and commercially available under the "Ficam" (brand) name (see also U.S. Pat. No. 3,736,338 to Fisons); 1-naphthalenol methyl carbamate, also known by its "trivial" name of "Carbaryl", and commercially available under the "Arylam", "Carylderm", "Dicarbam", "Seffein" and "Sevin" (brand) names (see also U.S. Pat. No. 2,903,478 to Union Carbide); and 2-(1-methyl ethoxy)phenol methyl carbamate, also known by its "trivial" name of "Propoxur", and commercially available under the "Baygon", "Bifex", "Blattanex", "Invisi-Gard", "Propyon", "Sendran", "Suncide" and "Unden" (brand) names (see also U.S. Pat. No. 3,111,539 to Bayer). (See, e.g., entry Nos. 1035, 1766 and 7737, respectively, in the text entitled "The Merck Index", 10th ed.)

For purposes of my present invention suitable inorganic toxicants include but are not limited to certain well-known stomach poisons, such as the arsenicals (i.e., any one of a variety of well-known arsenic-containing compounds), certain heavy metal-containing compounds, and certain fluorine-containing compounds, as well as boric acid, silica gel and sodium borate. (See, e.g., page 62 of the text entitled "Pesticides: Theory and Application" by George W. Ware.)

Insect growth regulators (IGRs), occasionally referred to as "biorationals", are rather specific chemicals which are presently believed to be generally environmentally "safe" Moreover, certain ones of the presently-known IGRs tend to closely resemble certain biological, organic-type chemicals produced by certain insects and/or plants. IGRs function by altering growth and development of arthropods. The observed effects of IGRs upon metamorphosis, upon reproduction, upon behavior, and upon embryonic, larval and nymphal development have, moreover, been reported in the literature. (See, e.g., page 62 of "Pesticides: Theory and Application" by George W. Ware.) A number of IGRs, found to be effective when utilized in very minute quantities, appear to have no undesirable effects on humans and wildlife. (Id.) Furthermore, it is well known that IGRs are typically nonspecific; and as a result, they are known to affect not only the target species of arthropod but also a variety of other arthropods as well. (Id.)

For purposes of my present invention, suitable insect growth regulators (IGRs) include but are not limited to: N-[[(4-chlorophenyl)amino]carbonyl]-2,6-difluorobenzamide (a known chitin-synthesis inhibitor), also known by its "trivial" name "Diflubenzuron", and commercially available under the "Difluron" and "Dimilin" (brand) names; 2,3,14,22,25-pentahydroxycholest-7-en-6-one ($C_{27}H_{44}O_6$) and 2,3,14,20,22,25-hexahydroxycholest-7-en-6-one ($C_{27}H_{44}O_7$), also known by their "trivial" names "alpha-Ecdysone" and "beta-Ecdysone", respectively, which are well-known insect-molting hormones that are used for the purpose of controlling the pupation of insects; 7-ethyl-9-(3-ethyl-3-methyloxiranyl)-3-methyl-2,6-nonadienoic acid methyl ester ($C_{18}H_{30}O_3$) and cis-10,11-epoxy-3,7,11-trimethyl-trans,-trans-2,6-tridecadienoic acid methyl ester ($C_{17}H_{28}O_3$), both generally described by the "trivial" term "Juvenile Hormone" (JH), each more particularly recognized (by those skilled in the art) by the abbreviations "C-18 JH" and "C-17 JH", respectively; 3,7,11-trimethyl-2,4-dodecadienoic acid 2-propynyl ester, also known by its "trivial" name "Kinoprene", and commercially available under the "Enstar" (brand) name (see also U.S. Pat. No. 3,833,635 to Zoecon); and 11-methoxy-3,7,11-trimethyl-2,4-dodecanoic acid 1-methylethyl ester, also known by its "trivial" name "Methoprene", and commercially available under the "Altosid", "Apex", "Kabat", and "Manta" (brand) names (see also U.S. Pat. Nos. 3,818,047 and 3,865,874, both to Zoecon). (See, e.g., entry Nos. 3125, 3470, 5111, 5150 and 5859, respectively, in "The Merck Index", 10th ed.; and pages 62–64 of "Pesticides: Theory and Application" by George W. Ware.) The term "Juvenile Hormone", as used in this application, includes: the so-called "JH mimic" and "JH analog" (JHA) IGRs, and their broader synonyms, the so-called "juvenoids" and "juvegens" (See, e.g., page 62 of "Pesticides: Theory and Application" by George W. Ware.)

Still further, and in addition to what was specifically identified hereinabove, certain other toxicants, particularly effective in controlling a variety of arthropods (except ants), in general, and suitable for purposes of my present invention include but are not limited to cypermethrin, other synthetic pyrethroids (such as permethrin, deltamethrin, alphamethrin, and cyphenothrin and the like), and natural pyrethrum. However, as was briefly noted immediately above, pyrethroids, which have been observed as being generally repellent to most ants at ever minute concentrations, would generally not be included in the formulations of my composition-of-matter when such is to be used to control the proliferation of ants and/or ant colonies.

What has been described herein is a novel dual emulsion and a method for producing the same. While my present invention has been described with reference to certain preferred embodiments, it is to be understood that my present invention is not to be limited to the preferred embodiments discussed herein. Indeed, those skilled in the art, upon reviewing my disclosure, will become aware of certain utility in the specific area of "powder technology", as well as various "powder technology" delivery systems. Accordingly, alternatives, changes and/or modifications will become apparent to those skilled in the pertinent prior art upon reading the foregoing description. Yet such alternatives, changes and/or modifications are to be considered as forming a part of my present invention insofar as such fall within the spirit and scope of the appended claims.

I claim:

1. A method of producing a stable dual emulsion, comprising the steps of:

combining water, a first liquid hydrocarbon solvent and an emulsifier, along with an effective amount of a finely-divided particulate material, in a mixing zone, to produce an oil-in-water emulsion having a viscosity of no more than about 200,000 centipoises, wherein the first liquid hydrocarbon solvent is selected from the group consisting of naphthas having a boiling point range of from 93° C. to 300° C., liquid isoparaffinic and normal paraffinic solvents, mineral oil, and mixtures thereof, and wherein the finely-divided particulate material is substantially homogeneously-dispersed throughout the oil-in-water emulsion;

combining a second liquid hydrocarbon solvent, an effective amount of water and an emulsifier, in a mixing zone, wherein the second liquid hydrocarbon solvent is selected from the group consisting of naphthas having a boiling point range of from 93° C. to 300° C., liquid isoparaffinic and normal paraffinic solvents, mineral oil, and mixtures thereof, thereby to produce a water-in-oil emulsion having a viscosity at 25° C. of from 1.0 cPs. to 20,000 cPs, and containing from 1.0 weight percent to 50.0 weight percent water, based on total weight of the thus-produced water-in-oil emulsion; and combining 100 parts-by-weight of the water-in-oil emulsion with from 0.01 parts-by-weight to 200 parts-by-weight of the oil-in-water emulsion, in a mixing zone, to produce a stable dual emulsion having a viscosity at 25° C., of from 100 cPs. to 20,000 cPs, and containing 10 weight percent to 60 weight percent water, based on total weight of the thus-produced stable dual emulsion, wherein the dual emulsion is characterized as being a water-in-oil emulsion.

2. The method of claim 1 wherein the finely-divided particulate material is selected form the group consisting of activate charcoal, calcined alumina, calcined ferric oxide, calcium metasilicate, calcium carbonate, diatomaceous silica, fumed silica, amorphous silica, hydrous magnesium silicate, hydrous aluminum silicate, anhydrous aluminum silicate, and combinations thereof.

3. The method of claim 1 wherein the finely-divided particulate material is a micro-silica having a particle size of about 0.01 microns to about 25 microns, an apparent bulk density of less than 21.0 pounds per cubic foot, and an apparent surface area of 275 to 320 square meters per gram.

4. The method of claim 1 wherein the stable dual emulsion further includes an effective amount of an arthropodicidally-active toxicant for controlling the proliferation of a preselected arthropod colony.

* * * * *